United States Patent
Khang et al.

(10) Patent No.: US 10,434,216 B2
(45) Date of Patent: Oct. 8, 2019

(54) ULTRA-THIN FILM SILK FIBROIN/COLLAGEN COMPOSITE IMPLANT AND MANUFACTURING METHOD THEREFOR

(71) Applicant: INDUSTRIAL COOPERATION FOUNDATION CHONBUK NATIONAL UNIVERSITY, Jeonju-si, Jeollabuk-do (KR)

(72) Inventors: Gil Son Khang, Daejeon (KR); Eun Young Kim, Jeonju-si (KR); Jae Won Yang, Gwangju (KR); Jeong Eun Song, Jeonju-si (KR); Se Rom Cha, Jindo-gun (KR)

(73) Assignee: Industrial Cooperation Foundation Chonbuk National University, Jeonju-si, Jeollabuk-Do (KR)

( * ) Notice: Subject to any disclaimer, the term of this patent is extended or adjusted under 35 U.S.C. 154(b) by 127 days.

(21) Appl. No.: 15/505,054

(22) PCT Filed: Jul. 10, 2015

(86) PCT No.: PCT/KR2015/007210
§ 371 (c)(1),
(2) Date: Feb. 17, 2017

(87) PCT Pub. No.: WO2016/027988
PCT Pub. Date: Feb. 25, 2016

(65) Prior Publication Data
US 2017/0266345 A1    Sep. 21, 2017

(30) Foreign Application Priority Data

Aug. 19, 2014  (KR) ........................ 10-2014-0107440

(51) Int. Cl.
*A61L 27/24* (2006.01)
*A61L 27/26* (2006.01)
*A61L 27/36* (2006.01)
*A61L 27/22* (2006.01)
*A61L 27/38* (2006.01)
*A61L 27/48* (2006.01)

(52) U.S. Cl.
CPC ............. *A61L 27/26* (2013.01); *A61L 27/222* (2013.01); *A61L 27/227* (2013.01); *A61L 27/24* (2013.01);
(Continued)

(58) Field of Classification Search
CPC ...... A61L 27/26; A61L 27/48; A61L 2430/16; A61L 27/222; A61L 27/227; A61L 27/24;
(Continued)

(56) References Cited

U.S. PATENT DOCUMENTS 5,002,582 A * 3/1991 Guire .................... A61F 2/0077
427/2.24
5,863,984 A * 1/1999 Doillon .................. A61L 27/48
424/423
(Continued)

FOREIGN PATENT DOCUMENTS

CN    101716375    *  6/2010
EP    2447055 A1    5/2012
(Continued)

OTHER PUBLICATIONS

Aramwit et al. (International Journal of Molecular Sciences 2010, 11, 2200-2211).*
(Continued)

*Primary Examiner* — Ernst V Arnold
(74) *Attorney, Agent, or Firm* — Knobbe Martens Olson & Bear LLP

(57) ABSTRACT

The present invention relates to an ultra-thin film silk fibroin/collagen composite implant for tissue engineering and a manufacturing method therefor. The ultra-thin film silk
(Continued)

fibroin/collagen silk fibroin/collagen composite implant according to the present invention has no cytotoxicity and can minimize the influence on cell growth, due to the combined use of a refined silk fibroin aqueous solution, collagen and various biomaterials, and thus can be widely used as an ultra-thin film implant for implanting.

9 Claims, 2 Drawing Sheets

(52) U.S. Cl.
CPC ....... *A61L 27/3604* (2013.01); *A61L 27/3808* (2013.01); *A61L 27/48* (2013.01); *A61L 2430/16* (2013.01)

(58) Field of Classification Search
CPC .... A61L 27/3604; A61L 27/3808; C08L 1/00; C08L 3/02; C08L 5/04; C08L 5/08; C08L 89/00; C08L 89/06
See application file for complete search history.

(56) References Cited

U.S. PATENT DOCUMENTS

| | | | | |
|---|---|---|---|---|
| 2003/0087433 | A1* | 5/2003 | Tsubouchi | A61K 8/64 435/391 |
| 2013/0240251 | A1* | 9/2013 | Kaplan | H01Q 7/00 174/254 |

FOREIGN PATENT DOCUMENTS

| | | |
|---|---|---|
| KR | 10-2010-0121169 A | 11/2010 |
| KR | 10-2011-0104584 A | 9/2011 |
| KR | 10-2011-0127324 A | 11/2011 |
| KR | 10-2012-0067831 A | 6/2012 |
| KR | 10-2013-0006834 A | 1/2013 |
| WO | WO-2007043255  * | 4/2007 |
| WO | 2014-011644 A1 | 1/2014 |

OTHER PUBLICATIONS

Madden et al. (Biomaterials 32 (2011) 4076-4084) (Year: 2011).*
Abstract of: Zhongguo Xiu Fu Chong Jian Wai Ke Za Zhi. Jul. 2014;28(7):903-8. (Year: 2014).*
Lu et al. (J Mater Sci: Mater Med 2008;19:629-634) (Year: 2008).*
English langauge Abstract of JP11228837 1999 2 pages (Year: 1999).*
English langague translation of KR20110104584 2011 8 pages (Year: 2011).*
International Search Report dated Oct. 1, 2015 of PCT/KR2015/007210 which is the parent application and its English translation—4 pages.

* cited by examiner

ULTRA-THIN FILM SILK FIBROIN/COLLAGEN COMPOSITE IMPLANT AND MANUFACTURING METHOD THEREFOR

TECHNICAL FIELD

The present invention relates to a composite implant for implanting having an ultra-thin film form obtained by preparing a solution including silk fibroin (or silk protein), collagen and optionally a biomaterial in a film form, and a method for manufacturing the same, and more particularly, to an implant for implanting manufactured by preparing an implantable film type implant in order to apply the same to organs requiring an ultra-thin film in a range of 4 to 10 μm.

BACKGROUND ART

Regeneration medicine and tissue engineering are typically proposed as an ideal solution to overcome limitations due to lack of tissues and/or organs for graft substitutes. The tissue engineering is a technique in which specific cells separated and cultured from a patient are adhered to an implant made of biocompatible/biodegradable material, and the implant is organized through biochemical stimulation using a bioactive factor or physical stimulation using a bioreactor.

In other words, the artificial organ engineered and manufactured according to the above method is similar to biotissues of a human body, thus to have a high potential ability as a graft substitute for autologous tissue implant. As described above, the tissue engineering may be defined with three elements including a cell, stimulant and implant. The present invention has focused on the implant, in particular, an ultra-thin silk composite implant manufactured by using biomaterials, and investigated characteristics thereof.

Since the silk has been used as a sawing yarn for several centuries, it is possible to have a role of favorable biomaterials in the tissue engineering applications. Korean Patent Laid-Open Publication No. 2010-0121169 relates to an artificial eardrum fabricated using silk protein and a manufacturing method thereof, and proposes that an implant obtained in the manufacturing process with addition of any additive may have a thickness of 80 to 120 μm thus to apply the same to a tissue that requires a thin film such as an eardrum. However, the above technique could not be used in a tissue that requires an ultra-thin film of 20 μm or less such as a cornea, hence having a limitation in applications.

Korean Patent Laid-Open Publication No. 2011-0104584 relates to a composite support including silk and collagen and a method for manufacturing the same. In this case, the above support may form a structure including a woven silk tube layer and a collagen layer inside the tube, thus to provide a three-dimensional support useable as a matrix for regeneration of ligaments and tendons, reconstruction of damaged muscles, or the like. However, the above technique involves limitations in applying the above support to ultra-thin films such as cornea, retina, eardrum, etc. and some applications requiring transparency.

Meanwhile, Bombyx mori (B. mori)-derived silk consists of two different proteins, that is, fibroin and sericin.

Herein, the fibroin is a protein constituting about 75% in silk cocoon and includes at most 90% of insoluble proteins such as glycine, alanine and serine. Further, the fibroin does not occur an immune reaction during in vivo transplant, may control a degree of degradation, and has excellent mechanical strength and good transparency to oxygen and water.

Further, silk fibroin supports adhesion and growth of human limbal stem cells and fibroblast cells, and is used in a wide range of applications such as a wound dressing agent, enzyme immobilization membrane, cell medium, artificial skin, soft contact lens, etc. Furthermore, many researchers have reported that a two-dimensional silk fibroin film could provide desired biological synthesis performance.

In addition, sericin constitutes the remaining 25% in the silk cocoon, but causes an occurrence of the immune reaction and allergic response, thus being typically used after a refining process of removing the sericin. However, sericin is a hydrophilic protein and has a strong polar chain, and further is a biodegradable material to provide a variety of advantages such as anticoagulation, antioxidation, and anti-wrinkling properties. Further, the researchers have recently reported that sericin can prevent cell apoptosis, inhibit cancer generation, reinforce adhesion and proliferation of fibroblast cells, and be applicable as a component of the cell medium.

Meanwhile, the above-described silk fibroin may be used in the tissue engineering by dissolving the refined silk fibroin in an organic solvent after lyophilizing, then, preparing the same into a film through a casting process. The prepared silk fibroin film may possibly contain the organic solvent residue remained therein, and the organic solvent residue toxically may act on the cell and the body in vivo during transplant thus to affect the adhesion and growth of the cells. Accordingly, it has been raised a requirement for an ultra-thin film composite implant for implanting, wherein the implant has no cytotoxicity, minimizes an effect on the cell growth, does not cause toxicity in vivo during transplant, and can be implanted in any case where needs the ultra-thin film such as corneal endothelial transplantation.

The above subject matters described as a background of art have been proposed to more concretely understand the background of the present invention only, however, it should not be construed or recognized to correspond to the prior art known to those skilled in the art to which the present invention pertains.

DISCLOSURE

Technical Problem

Any conventional silk fibroin solution was used in such a way that powders obtained by lyophilizing the refined silk fibroin is dissolved in an organic solvent. However, the present inventors did not use any organic solvent but directly used the refined silk fibroin solution, thereby preventing the organic solvent residue from toxically acting on the cell and the body in vivo, thereby minimizing effects on the adhesion and growth of cell and affinity with surrounding tissues. Further, a biomaterial is used for providing a structural environment for adhesion and proliferation of graft cells and cell delivery, as well as, when an implant is manufactured by mixing silk fibroin and collagen, an ultra-thin film can be prepared by an acid component used for dissolving the collagen, and the prepared film does not significantly affect the transparency, thereby exhibiting more excellent properties in adhering and proliferating the tissue cell selected from a group consisting of corneal epithelium, corneal endothelium, retina, eardrum and oral cavity. Therefore, the inventors have found the above results and completed the present invention.

Accordingly, it is an object of the present invention to provide a silk fibroin/collagen composite implant for implanting.

Another object of the present invention is to provide a method for manufacturing the silk fibroin/collagen composite implant for implanting.

Other objects and advantages of the present invention will be more obviously understood by the following detailed description, claims and accompanying drawings.

Technical Solution

In order to achieve the above objects, according to an aspect of the present invention, there is provided a silk fibroin/collagen composite implant, including a film obtained by preparing a solution including silk fibroin and collagen so as to have an ultra-thin film form.

In addition, according to another aspect of the present invention, there is provided a method for manufacturing a silk fibroin/collagen composite implant, the method including: (i) dissolving collagen in acid; (ii) mixing the collagen solution prepared in the step (i) with a silk fibroin solution including 1 to 10 v/v % of sericin which is refined from silkworm cocoons or silk fibers; (iii) casting the silk fibroin-collagen mixture solution to form a film and drying the same; (iv) cross-linking and crystallizing the dried film; and (v) drying the cross-linked and crystallized film to manufacture an ultra-thin film transparent silk fibroin/collagen composite implant.

Advantageous Effects

The present invention has characteristics and advantages summarized as follows:

(i) According to the present invention, there is provided an ultra-thin film transparent composite implant for implanting by using a biomaterial;

(ii) In addition, according to the present invention, there is provided a method for manufacturing the ultra-thin film silk fibroin/collagen composite implant; and (iii) The ultra-thin film silk fibroin/collagen silk fibroin/collagen composite implant according to the present invention may be used for a variety of transplant operations requiring an ultra-thin film. In particular, a tissue engineering-based bio-cornea may be fabricated by applying the inventive composite implant as a substrate for corneal endothelial cells, thereby effectively proposing potential replacement of insufficiently donated cornea.

EMBODIMENTS

Figure 1:
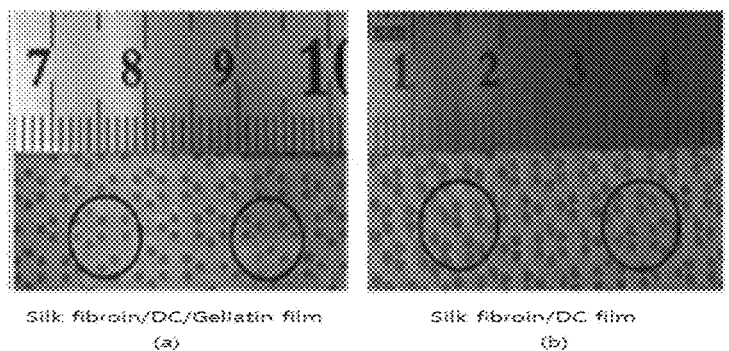
FIG. 1 is photographs visibly observed and measurement results of transparency of: (a) a silk fibroin/collagen/gelatin composite implant film (Example 1-1); and (b) a silk fibroin/collagen composite implant film (Example 2), which are manufactured by a method according to the present invention.

Hereinafter, the present invention will be described in detail as an embodiment.

The composite implant manufactured of a conventional silk fibroin was used in a film form by refining the silk fibroin, lyophilizing the same, then dissolving the lyophilized powders in an organic solvent to prepare a solution, and then, processing the solution through a casting process to prepare the film. This involved a limitation in applications since the organic solvent residue may toxically act on the cells thus to affect the adhesion and growth of cells. Accordingly, in order to improve the above limitation, the present inventors have tried to develop a composite implant using an alternative silk fibroin different from the conventional ones.

As a result, when preparing a silk fibroin solution, any organic solvent was not used after refining silkworm cocoons or silk fibers, thereby overcoming the above problem due to the organic solvent residue. Further, the present inventors have found that, when using the refined silk fibroin solution without completely removing sericin, that is, containing sericin in a concentration of 1 to 10 v/v %, the cells could be efficiently adhered and regenerated (grown).

Thereby, according to an aspect of the present invention, there is provided a silk fibroin/collagen composite implant including a film obtained by preparing a solution including silk fibroin and collagen so as to have an ultra-thin film form. Herein, the solution may further include a biomaterial.

The "collagen" used in the present invention is preferably extracted from flippers of a duck by using an acid solution. However, the collagen may also be extracted from other animals such as a rat's tail, chicken, pig, etc. other than the flippers of the duck, or collagen commercially available in a market may be used, and it is not particularly limited thereto.

The above-described acid solution may include at least one selected from a group consisting of acetic acid, citric acid and lactic acid, however, most preferably, acetic acid.

Further, the term of "biomaterial" used in the present invention generally refers to a natural or synthetic polymer which is non-toxic to a human body, chemically inactive and has no immunogenicity.

The biomaterial is a material that may be mixed with silk fibroin to prepare an implant. For example, synthetic materials such as polyvinyl pyrrolidone (PVP), carboxymethyl cellulose (CMC), etc. have water absorbency increased up to 100 times, thus there is a difficulty in application as an ultra-thin film implant for implanting.

Therefore, according to a preferred embodiment of the present invention, the biomaterial used herein may include, for example: muco-polysaccharides including hyaluronic acid; natural proteins including at least one selected from a group consisting of gelatin and collagen; linear polysaccharides including at least one selected from a group consisting of chitosan, starch and cellulose; seaweed-derived polysaccharides including alginic acid; polysaccharides obtained by fermentation of bacteria including at least one selected from gellan gum and flurane; and low molecular weight polysaccharides including cyclodextrin.

The above biomaterial may facilitate adhesion, growth and proliferation of graft cells and provide desired a microenvironment wherein the cells may be structurally stably positioned, therefore, be effective for adhesion and proliferation of the graft cells. Further, when mixing the biomaterial with silk fibroin to prepare an implant, there is an advantage that a composite implant may be manufactured without any significant influence upon an ultra-thin film and transparency.

In this regard, the silk fibroin/collagen composite implant may have a form of ultra-thin film, and it is preferable that the film has a more reduced thickness. However, since the implant should be easily handled and, in order to culture and deliver a graft cell to an implant site, the film preferably has a thickness of 4 to 10 μm.

According to another aspect of the present invention, there is provided a method for manufacturing a silk fibroin/collagen composite implant, which includes:

(i) dissolving collagen in acid;

(ii) mixing the collagen solution prepared in the step (i) with a silk fibroin solution including 1 to 10 v/v % of sericin refined and obtained from silkworm cocoon or silk fiber;

(iii) casting the silk fibroin-collagen mixture solution to form a film then drying the same;

(iv) cross-linking and crystallizing the dried film; and (v) drying the cross-linked and crystallized film to manufacture an ultra-thin film transparent silk fibroin/collagen composite implant.

According to a preferred embodiment of the present invention, the manufacturing method of the present invention may further include, after the step (v), (vi) seeding tissue cells selected from a group consisting of corneal epithelium, corneal endothelium, retina, eardrum and oral cavity on the transparent silk fibroin/collagen composite implant.

The manufacturing method of the present invention will be described in detail according to each step as follows:

(i) Dissolving Collagen in Acid

In the present invention, collagen may be prepared by dissolving in 0.1 to 1N acid solvent. Preferably, the collagen is prepared by dissolving in 0.2 to 0.8N acid solvent, and more preferably, in 0.4 to 0.6N acid solvent. Most preferably, the collagen is prepared by dissolving in 0.5N acid solvent.

The solvent is not particularly limited so far as the collagen could be dissolved therein. Preferably, acetic acid, citric acid, lactic acid, etc., is used. More preferably, the acetic acid is used.

Further, the collagen may be extracted from the rat's tail, chicken, pig, etc., preferably, flippers of a duck having a high collagen content are used.

(ii) Mixing Collagen in Refined Silk Fibroin Solution

In the present invention, the collagen is dissolved in 0.5N acid solvent, that is, in acetic acid, then, 1 to 10 wt. % of refined silk fibroin solution is added to the above solution in a micro-tube, followed by mixing the same, so as to reach a total volume of 0.5 to 4 mL. Preferably, the mixing is executed to reach a total volume of 1 to 3 mL and, more preferably, a total volume of 2 mL.

Herein, the refined silk fibroin solution includes 1 to 10 v/v % of sericin and may be prepared by controlling a boiling time during boiling silk cocoons. More particularly, the refined silk fibroin solution is obtained by placing silkworm cocoons or silk fibers in a sodium carbonate solution ($Na_2CO_3$), boiling and drying the solution to obtain dried silk, and dissolving the dried silk in a lithium bromide (LiBr) solution, dialyzing this solution through a dialysis membrane having a fractional molecular weight of 3500 for 3 days, then, filtering the same.

In addition, the silk fibroin and the collagen are preferably mixed in a volume ratio of 1 to 3:3 to 1. Herein, as an amount of silk fibroin is increased, it is more difficult to realize an ultra-thin film thickness. Further, if a content of collagen is too high, it is not easy to form the film. Therefore, it is preferable to use the above components within the above-defined range of volume ratios.

Furthermore, the collagen is more preferably included in an amount of 25 v/v % or more to a total volume of the solution including collagen and silk fibroin.

(ii-1) Addition of Biomaterial to Silk Fibroin-Collagen Mixture Solution

Preferably, the mixture solution of the refined silk fibroin solution and collagen extracted from the flippers of a duck and the biomaterial are mixed in a volume ratio of 1 to 3:1 then used. If these materials are mixed in a volume ratio out of the above range, the solution may not be formed in a film form during manufacturing the film. Therefore, it is preferable to use these materials within the above range.

(iii) Formation of Film by Casting the Silk Fibroin-Collagen Mixture Solution

The solution including the silk fibroin, collagen and biomaterial prepared in the step (ii) is casted by pouring this solution on a glass dish having a diameter of 10 to 100 mm, preferably, a diameter of 30 to 70 mm, and more preferably, a diameter of 50 mm, followed by being dried at room temperature for 24 to 120 hours, preferably, 48 to 96 hours. More preferably, the above solution is dried at 10 to 35° C. for 72 hours, preferably 15 to 30° C., and more preferably, 20 to 25° C.

(iv) Cross-Linking and Crystallization of Dried Film 1-ethyl-3-(3-dimethylaminopropyl)carbodiimide having 0.1 to 3% concentration is poured on the film formed in the step (iii), and cross-linked at room temperature for 24 hours. 1-ethyl-3-(3-dimethylaminopropyl)carbodiimide having 0.5 to 2% concentration is preferably used, and 1-ethyl-3-(3-dimethylaminopropyl)carbodiimide having 1% concentration is more preferably used. Other than the 1-ethyl-3-(3-dimethylaminopropyl)carbodiimide, EDC/N-hydroxysuccinimide or 2-chloro-1-methylpyridinium iodide may also be used to cross-link the same.

Following this, the film including the cross-linked collagen is treated using 100% methanol for 1 day to crystallize the silk fibroin. Instead of 100% methanol, 90% methanol or ethanol may also be used. The room temperature condition may refer to a temperature range of 10 to 35° C. for drying. Preferably, the drying is conducted in a temperature range of 15 to 30° C. and, more preferably, 20 to 25° C., while the time condition for cross-linking may range from 12 to 36 hours, and more preferably, the cross-linking is conducted for 24 hours.

The cross-linked and crystallized silk fibroin/collagen film is treated using 50 to 100% methanol to separate the film from the glass dish. 70 to 100% methanol is preferably used, and more preferably, 100% methanol is used to treat the film. Further, the film may be treated with ethanol to separate it from the glass dish. Since the film formed without cross-linking may be easily dissolved and disappeared in a water soluble solution, a minimum period of time for culturing the cells cannot be secured and there is a difficulty in handling the film.

(v) Drying Cross-Linked and Crystallized Film to Manufacture Ultra-Thin Film Transparent Silk Fibroin/Collagen Composite Implant The film formed in the step (iv) is dried at room temperature for 24 to 120 hours. Preferably, the drying is conducted for 48 to 96 hours. More preferably, the film is dried at 10 to 35° C. for 72 hours, preferably, at 15 to 30° C., and more preferably, 20 to 25° C., then, stored in a desiccator. The formed film is prepared by sterilizing with ethylene oxide gas. Alternatively, the film may also be sterilized using gamma-ray, alcohol, chloroform, or the like.

(vi) Seeding Tissue Cells on the Formed Ultra-Thin Transparent Film

To the sterilized ultra-thin transparent film formed in the step (v), tissue cells such as corneal epithelial cells, skin epithelial cells, fibroblast cells, vascular endothelial cells, etc., as a representative example, corneal endothelial cells are seeded at a cell density per unit area ranging from 50 to 1000 cell/mm$^2$. Preferably, the cells are seeded at a cell density of 200 to 700 cell/mm$^2$, and more preferably, at a cell density of 500 cell/mm$^2$. Preferably, culturing conditions include a temperature of 20 to 40° C., a carbon dioxide concentration of 1 to 10% and a time period of 30 minutes to 10 days. In a case of seeding at a cell density of 500 cell/mm$^2$, the culturing is preferably conducted for 1 day.

The ultra-thin transparent film formed in the process according to the present invention may be prepared to be applicable to not only the cornea but also any implant site requiring such an ultra-thin film or transparency.

Hereinafter, the present invention will be described in more detail by means of the following examples. However, these examples are proposed for illustrating the present invention only, and it should be understood that the scope of the present invention is not limited thereto.

Example 1

Examples 1-1 to 1-3

(i) Dissolving Collagen Extracted from Flippers of a Duck in Acid.

1 g of collagen extracted from the flippers of a duck was dissolved in 10 mL of 0.5N acetic acid, thereby preparing 1% collagen solution.

(ii) Mixing Collagen with Refined Silk Fibroin Solution

The 1% collagen solution was poured in a micro-tube and mixed with 6% refined silk fibroin solution so as to reach a total volume of 2 mL. Herein, the silk fibroin and the collagen were mixed in a volume ratio of 1 to 3:3 to 1. In particular, the products in Examples 1-1, 1-2 and 1-3 were prepared in volume ratios of 3:1, 1:1 and 1:3, respectively.

In this case, the refined silk fibroin solution used in the examples was obtained by placing silk cocoons in 0.02N sodium carbonate solution ($Na_2CO_3$), boiling the solution to dry the same, dissolving again the dried silk in 9.3M lithium bromide (LiBr) solution, dialyzing the mixture through a dialysis membrane having a fractional molecular weight of 3500 for 3 days while changing water every 12 hours, and then, filtering the product.

(ii-1) Adding Biomaterial to the Silk Fibroin/Collagen Mixture Solution to Prepare a Mixture Solution 1 mL of sample was obtained from 2 mL of 1% collagen/ 6% silk fibroin solution prepared in the step (ii), mixed with 1 mL of gelatin, poured into a micro-tube, followed by mixing the same in a ratio of 1:1 so as to reach a total volume of 2 mL.

(iii) Forming a Film from the Mixture Solution Including Silk Fibroin/Collagen/Biomaterial The silk fibroin/collagen/gelatin mixture solution was poured on a glass dish having a diameter of 50 mm, followed by drying the same at room temperature for 48 hours.

(iv) Cross-Linking and Crystallization of Dried Film

After adding 1% 1-ethyl-3-[3-dimethylaminopropyl]carbodiimide solution to the dried silk fibroin/collagen/gelatin film, the mixture was subjected to cross-linking at room temperature overnight. The silk fibroin-collagen-gelatin film cross-linked as described was treated with 100% methanol, thereby separating the film from the glass dish.

(v) Manufacturing Ultra-Thin Film Transparent Composite Implant by Drying the Cross-Linked and Crystallized Film The silk fibroin/collagen/gelatin film was dried at room temperature for 72 hours, thereby manufacturing a final ultra-thin film transparent silk fibroin/collagen composite implant. The film manufactured above was prepared by sterilizing with ethylene oxide gas.

(vi) Seeding Corneal Endothelial Cells

Corneal endothelial cells separated from a rabbit were seeded on the prepared film sterilized with ethylene oxide gas at a cell density of 500 cells/mm$^2$, followed by culturing the same for one day. In this case, the seeded cells were cultured at 37° C., and a condition of 5% carbon dioxide concentration.

Example 2

The silk fibroin/collagen composite implant film was manufactured by the same procedures as described in the examples, except that step (ii-1) was not executed.

Comparative Example 1

The silk fibroin/collagen/biomaterial composite implant film was manufactured by the same procedures as described in Example 1, except that the silk fibroin solution used in the step (ii) was prepared by dissolving the refined silk fibroin in an organic solvent (hexa-fluoro-isopropanol). More particularly, a method for preparing the silk fibroin solution used in Comparative Example 1 will be described as follows. After putting silk cocoons in 0.02N sodium carbonate solution ($Na_2CO_3$), the solution was boiled to dry silk and the dried silk was dissolved again in 9.3M lithium bromide solution, dialyzed through a dialysis membrane having a fractional molecular weight of 3500 for 3 days while changing water every 12 hours, and filtered. The filtered product was again dialyzed and treated by pouring a silk solution filtered through a gauze in a plastic dish, followed by treating the same at −80° C. for 24 hours. Thereafter, the treated product was lyophilized till completely dried. This lyophilized product was dissolved in hexa-fluoro-isopropanol as an organic solvent to prepare a solution and used.

Comparative Example 2

The silk fibroin film was formed by the same procedures as described in Example 1, except that the collagen solution in the step (ii) and the biomaterial in the step (ii-1) were not mixed.

Comparative Example 3

A transparent PLGA film was formed using a synthesized biomaterial, that is, polylactide glycolide copolymer (PLGA) which obtained the approval of the Food and Drug Administration (FDA) in United States.

Experimental Example 1: Determination of Transparency—Visible Observation

Transparency of each of the silk fibroin/collagen/gelatin composite implant film manufactured in Example 1-1 and the silk fibroin/collagen composite implant film manufactured in Example 2 was visibly observed and results thereof are shown in FIGS. 1(a) and 1(b). From the visible observation, it could be found that these films have high transparency and, regardless of whether collagen or gelatin is included, it could be seen that the transparency visibly observed was desirably maintained.

Experimental Example 2: Measurement of Thickness of Composite Implant (Film)

In order to measure a thickness of the film, each film was completely dried. After coating the film with osmium, observation was carried out using a field-emission scanning electron microscope (FE-SEM, SUPRA 40VP, Carl Zeiss, Germany) and results thereof are shown in FIG. 2.

Figure 2:
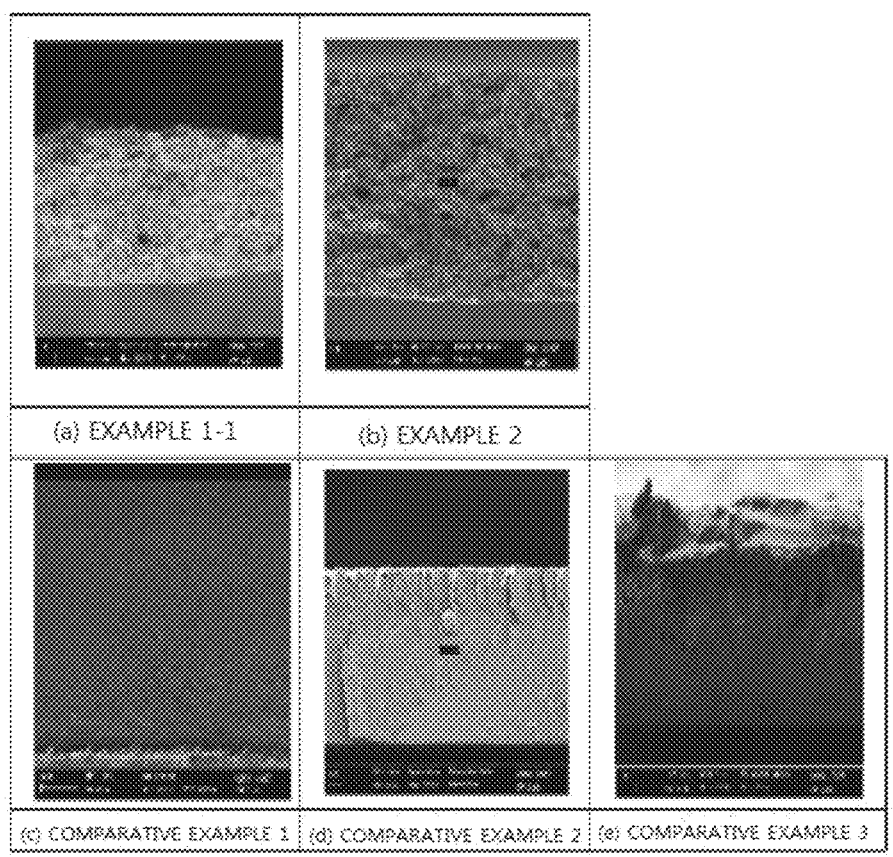
FIG. 2 is photographs illustrating cross-sections of the films observed by means of a field emission scanning electron microscope (FE-SEM), in order to measure a thickness of each of the composite implant films manufactured in the examples and comparative examples.

As shown in FIG. 2, it was found that the film manufactured in Example 1-1 has a thickness in a range of 4 to 7 µm (5.53±0.45 µm), while the film manufactured in Example 2 has a thickness in a range of 5 to 10 µm (8.0±0.3 µm).

On the other hand, it was found that Comparative Example 1 has a thickness of 40 to 100 µm (50.0±0.3 µm), Comparative Example 2 has a thickness of 15 to 20 µm (17.50±0.5 µm), and Comparative Example 3 has a thickness of 90 to 120 µm (105.0±4.5 µm), respectively.

Further, as a result of observing a cross-section of the formed film, it was found that Example 1-1 and Example 2 have a number of pores and a lamellar structure. On the other hand, Comparative Example 1 did not demonstrate any lamellar structure and, although some pores are included, the number of pores is lower than those in the examples. Comparative Example 2 demonstrated a small porous structure but did not have any lamellar structure. Further, Comparative Example 3 did not have pores but demonstrated a smooth lateral side. Based on such the observed results of the cross-section of the film, it could be indirectly understood that the examples show the most excellent film transparency.

Experimental Example 3: Assessment of Biocompatibility and Proliferation

Figure 3:
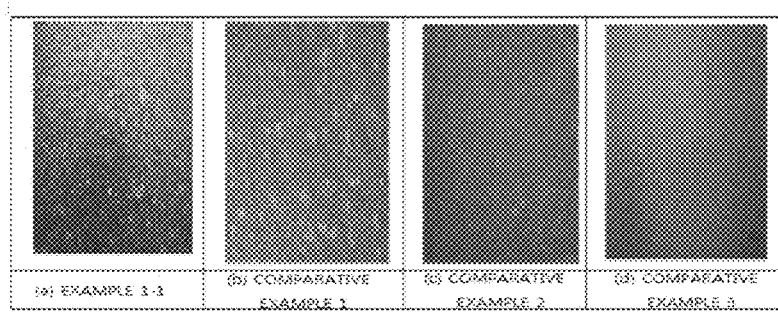
FIG. 3 is photographs observed through the FE-SEM to monitor the adhesion of rabbit corneal endothelial cells and cell morphology, in regard to the composite implant films manufactured in Example 1-1 and Comparative Examples 1 to 3.

Experimental Example 3-1: Observation of Adhesion of Rabbit Corneal Endothelial Cell and Cell Morphology In order to identify a relationship between the manufactured ultra-thin film implant and the cells, first generation corneal endothelia cells separated from a rabbit were seeded at a cell density of 500 cells/mm$^2$ and cultured at 37° C. under a carbon dioxide concentration of 5% for 1 day to determine a correlation with the cells. For this purpose, adhesion of rabbit corneal endothelial cells and a shape of the cells were observed through the FE-SEM and results thereof are shown in FIG. 3. FIG. 3(a) illustrates the result of cell proliferation in the ultra-thin silk fibroin/collagen composite implant film manufactured in Example 1, which has demonstrated active proliferation of cells. Further, it could be seen that a morphological specificity of the corneal endothelial cells has been well maintained.

On the other hand, the films formed in Comparative Examples 1 to 3 demonstrated that the cells were well grown but a size of the cells was a little increased. More particularly, the corneal endothelial cells generally keep a size of average 10 µm in the body and, if surrounding conditions are varied or not suitable or due to different causes, the corneal endothelial cells become enlarged and lapse a hexagonal shape. For Comparative Examples 1 to 3, it was found that the corneal endothelial cells cultured in each of the films have deteriorated abilities in adhesion, proliferation and keeping inherent features, compared to those of Example 1 and 2 including collagen. On the other hand, the results of Example 1-1 demonstrated that the size and features of the cells are similar to those of the corneal endothelial cells in the body and are well maintained. From these results, it could be understood that the composite film of the present invention has preferable biocompatibility.

Experimental Example 3-2: Measurement 2 of Optical Intensity (Assessment of Proliferation)

Figure 4:
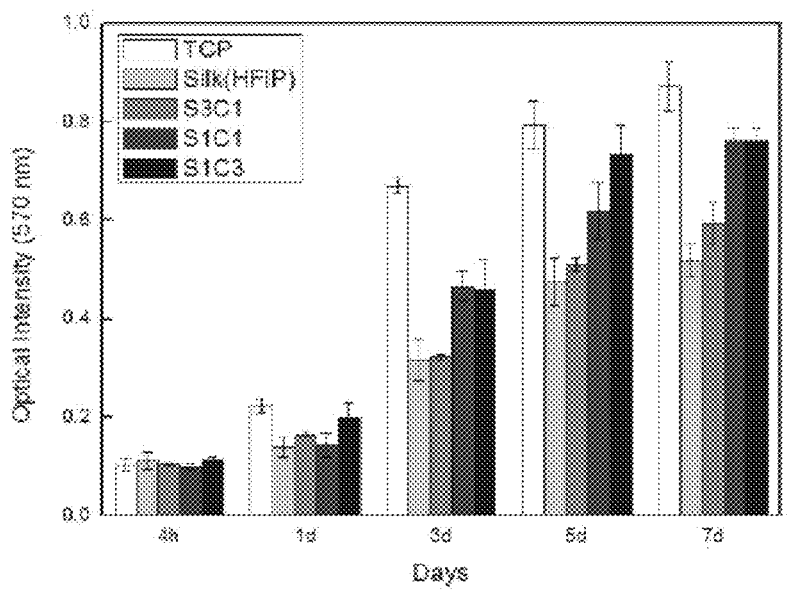
FIG. 4 is a graph illustrating compared results of cell proliferations (cultured for 7 days) in the composite implant films between Examples 1-1 to 1-3 and Comparative Example 1.

In order to assess a proliferation rate of seeded cells, the proliferation of corneal endothelial cells implanted in Experimental Example 3-1 on each of the films manufactured in Examples 1-1 to 1-3, Comparative Example 1, and a positive control (TCP) was observed up to 7 days. In particular, in order to assess the proliferation rate, an optical intensity was measured at 570 nm and results thereof are shown in FIG. 4. In this case, tissue culture polystyrene (TCP) corresponds to the positive control on which the cells are well proliferated. From the above experiment, it could be understood how fast the cells seeded on the film are proliferated.

The result shown in FIG. 4 demonstrated that the film in the examples of the present invention achieves more excellent cell growth, compared to the film manufactured in Comparative Example 1 with using a silk fibroin solution prepared by dissolving the refined silk fibroin in an organic solvent. As a content of collagen is increased, the cell proliferation rate was improved. Further, it was observed that the film of the present invention has a higher proliferation rate than the organic solvent-based silk fibroin film.

Therefore, it could be seen that the silk fibroin/collagen composite implant of the present invention is transparent in a film form, has an ultra-thin film having a very small thickness of 4 to 10 µm, and excellent performance in correlation with the cells, therefore, are preferably used as an implant on which various tissue cells including the corneal endothelial cells can be implanted.

In other words, the present invention uses any conventional refined silk fibroin without dissolving the same in an organic solvent, thereby minimizing influence of the organic solvent residue upon adhesion and growth of the cells due to the organic solvent residue toxically affecting the cells. In addition, by using the biomaterial, it is possible to provide a structural environment for adhesion and proliferation of the graft cells and cell delivery. Further, when an implant is manufactured using a mixture of silk fibroin and collagen, there is no significant influence upon an ultra-thin film and transparency. Accordingly, the implant of the present invention is favorable to the adhesion and proliferation of any tissue cell selected from a group consisting of corneal epithelium, corneal endothelium, retina, eardrum and oral cavity, which requires the implant having a thickness of 4 to 10 µm.

While the present invention has been described with reference to the preferred embodiments and modified examples, the present invention is not limited to the above-described specific embodiments and the modified examples, and it will be understood by those skilled in the related art that various modifications and variations may be made there without departing from the scope of the present invention as defined by the appended claims, as weal as these modifications and variations should not be understood separately from the technical spirit and prospect of the present invention.

The invention claimed is:

1. A method of manufacturing a silk fibroin-collagen composite film, the method comprising:
mixing a silk fibroin solution and a collagen solution to provide a liquid mixture comprising both silk fibroin and collagen;
applying, on a surface, the liquid mixture to provide a liquid layer comprising both silk fibroin and collagen;
subjecting the liquid layer to drying to provide a dried layer comprising both silk fibroin and collagen;
subjecting the dried layer to cross-linking of collagen therein to provide a cross-linked layer comprising both silk fibroin and cross-linked collagen; and
subsequently subjecting the cross-linked layer to crystallization of silk fibroin therein to provide a silk fibroin-collagen composite film comprising both silk fibroin crystals and cross-linked collagen.

2. The method of claim 1, wherein subjecting collagen of the dried layer to a cross-linking reaction comprises contacting the dried layer with a solution of 1-ethyl-3-(3-dimethylaminopropyl)carbodiimide, EDC/N-hydroxysuccinimide, or 2-chloro-1-methylpyridinium iodide in a concentration of 0.1 to 3%.

3. The method of claim 1, wherein subjecting silk fibroin in the cross-linked layer to crystallization of silk fibroin comprises contacting the cross-linked layer with methanol or ethanol.

4. The method of claim 1, further comprising:
subsequently to subjecting silk fibroin in the cross-linked layer to crystallization of silk fibroin, separating the silk fibroin-collagen composite film from the surface.

5. The method according to claim 1, wherein the silk fibroin solution comprises 1 to 10 v/v % of sericin such that the liquid mixture further comprises sericin in addition to silk fibroin and collagen.

6. The method according to claim 1, wherein the liquid mixture further comprises hyaluronic acid.

7. The method according to claim 1, wherein the liquid mixture further comprises a biomaterial.

8. The method according to claim 1, further comprising seeding corneal endothelium in the silk fibroin/collagen composite film.

9. A method for manufacturing a corneal endothelial transplantation implant comprising:
performing the method of claim 1 to provide a silk fibroin-collagen composite film comprising both silk fibroin crystals and cross-linked collagen therein;
seeding corneal endothelium on the silk fibroin-collagen composite film; and
culturing the corneal endothelium in the silk fibroin-collagen composite film to provide a corneal endothelial transplantation implant comprising the silk fibroin-collagen composite film and cultured corneal endothelium.

* * * * *